(12) United States Patent
Martin et al.

(10) Patent No.: US 10,434,264 B2
(45) Date of Patent: Oct. 8, 2019

(54) NEEDLE ASSEMBLY FOR MIXING OF SUBSTANCES

(71) Applicant: Becton, Dickinson and Company, Franklin Lakes, NJ (US)

(72) Inventors: Frank Martin, Durham, NC (US); Richard J. Klug, Roxboro, NC (US); M. Ishaq Haider, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/681,161

(22) Filed: Aug. 18, 2017

(65) Prior Publication Data
US 2017/0340839 A1    Nov. 30, 2017

Related U.S. Application Data

(63) Continuation of application No. 13/810,675, filed as application No. PCT/US2010/042876 on Jul. 22, 2010, now Pat. No. 9,775,956.

(51) Int. Cl.
*A61M 5/32* (2006.01)
*A61M 5/24* (2006.01)
*A61M 5/34* (2006.01)

(52) U.S. Cl.
CPC ......... *A61M 5/3294* (2013.01); *A61M 5/2448* (2013.01); *A61M 5/346* (2013.01); *A61M 5/347* (2013.01); *A61M 2005/2474* (2013.01)

(58) Field of Classification Search
CPC .. A61M 5/3294; A61M 5/2448; A61M 5/346; A61M 5/347

USPC ........................................................... 604/82
See application file for complete search history.

(56) References Cited

U.S. PATENT DOCUMENTS

| | | | |
|---|---|---|---|
| 2,778,360 A | 1/1957 | Miskel | |
| 2,864,366 A | 12/1958 | Miskel | |
| 3,757,779 A | 9/1973 | Rovinski | |
| 4,043,335 A | 8/1977 | Ishikawa | |
| 4,061,143 A * | 12/1977 | Ishikawa | A61M 5/3145 604/190 |
| 4,365,626 A * | 12/1982 | House | A61M 5/002 604/190 |
| 4,424,057 A | 1/1984 | House | |

(Continued)

FOREIGN PATENT DOCUMENTS

| DE | 2624328 A1 | 12/1977 |
|---|---|---|
| EP | 1631345 A1 | 3/2006 |

(Continued)

*Primary Examiner* — Phillip A Gray
(74) *Attorney, Agent, or Firm* — Dickinson Wright PLLC

(57) ABSTRACT

In one aspect of the invention, a needle assembly is provided, including: a body having a proximal end, a distal end, and a channel located therebetween, the body being configured to be mounted to an injector; a needle fixed to the body, the needle having proximal and distal ends, the distal end extending distally from the distal end of the body and being formed for insertion into a patient, the proximal end of the needle being in communication with the channel; and, a filter disposed in the channel proximally of the proximal end of the needle. Advantageously, a needle assembly is provided which permits mixing of at least two substances in preparation for injection, without modification to the associated injector.

9 Claims, 2 Drawing Sheets

(56) References Cited

U.S. PATENT DOCUMENTS

| | | | |
|---|---|---|---|
| 4,781,683 | A | 11/1988 | Wozniak et al. |
| 4,968,299 | A | 11/1990 | Ahlstrand et al. |
| 5,330,426 | A | 7/1994 | Kriesel et al. |
| 2002/0049406 | A1 | 4/2002 | Hill et al. |
| 2004/0138611 | A1 | 7/2004 | Griffiths et al. |

FOREIGN PATENT DOCUMENTS

| | | |
|---|---|---|
| JP | 4891797 B2 | 2/1972 |
| JP | 58143824 | 8/1983 |
| JP | 6052846 | 3/1985 |
| JP | 10502559 | 3/1998 |
| JP | 11089934 | 4/1999 |
| JP | 2001121005 | 5/2001 |
| JP | 2001523490 | 11/2001 |
| JP | 2002504403 | 2/2002 |
| JP | 2005537106 A | 12/2005 |
| JP | 2008526300 | 7/2008 |
| JP | 2012530578 A | 12/2012 |
| WO | WO-9943369 | 9/1999 |

\* cited by examiner

NEEDLE ASSEMBLY FOR MIXING OF SUBSTANCES

CROSS-REFERENCE TO RELATED APPLICATION

This application is a continuation of U.S. patent application Ser. No. 13/810,675, filed Jan. 17, 2013, which is the U.S. national stage of international patent application number PCT/US10/42876, filed Jul. 22, 2010. Each of the disclosures of these applications is hereby incorporated herein by reference in its entirety

FIELD OF THE INVENTION

This invention relates to needle assemblies for mixing of at least two substances in preparation for medical injection.

BACKGROUND OF THE INVENTION

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder form that require reconstitution.

In addition, drugs may be provided as multipart systems which require mixing prior to administration. For example, one or more liquid (e.g., flowable (slurry or liquid)) components, and/or dry (e.g., powdered or granular) components may be provided in a drug container or delivery device which require mixing prior to administration. The components can be mixed and used to form various administratable drugs, such as insulin.

Prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. U.S. Pat. No. 4,874,381 to Vetter is directed to an injector having a barrel configured for mixing, while U.S. Pat. No. 4,968,299 to Ahlstrand et al. is directed to a drug cartridge having a barrel configured for mixing. Both Vetter et al. and Ahlstrand et al. disclose typical configurations for mixing where a bypass channel is formed in the barrel of the device. As such, the device must be specifically configured for mixing.

SUMMARY OF EMBODIMENTS OF THE INVENTION

In one aspect of the invention, a needle assembly is provided, including: a body having a proximal end, a distal end, and a channel located therebetween, the body being configured to be mounted to an injector; a needle fixed to the body, the needle having proximal and distal ends, the distal end extending distally from the distal end of the body and being formed for insertion into a patient, the proximal end of the needle being in communication with the channel; and, a filter disposed in the channel proximally of the proximal end of the needle. Advantageously, a needle assembly is provided which permits mixing of at least two substances in preparation for injection, without modification to the associated injector.

Another aspect of the invention provides a needle assembly, including: a body having a proximal end, a distal end, and a channel located therebetween, the body being configured to be mounted to an injector; a needle fixed to the body, the needle having proximal and distal ends, the distal end extending distally from the distal end of the body and being formed for insertion into a patient, the proximal end of the needle being in communication with the channel; and a rupturable membrane disposed in the channel proximally of the proximal end of the needle.

As used herein, the term "distal", and derivatives thereof, shall refer to a direction towards a patient during use, and the term "proximal", and derivatives thereof, shall refer to a direction away from a patient during use.

These and other features of the invention will be better understood through a study of the following detailed description and accompanying drawings.

DETAILED DESCRIPTION OF EMBODIMENTS OF THE PRESENT INVENTION

Figure 1:
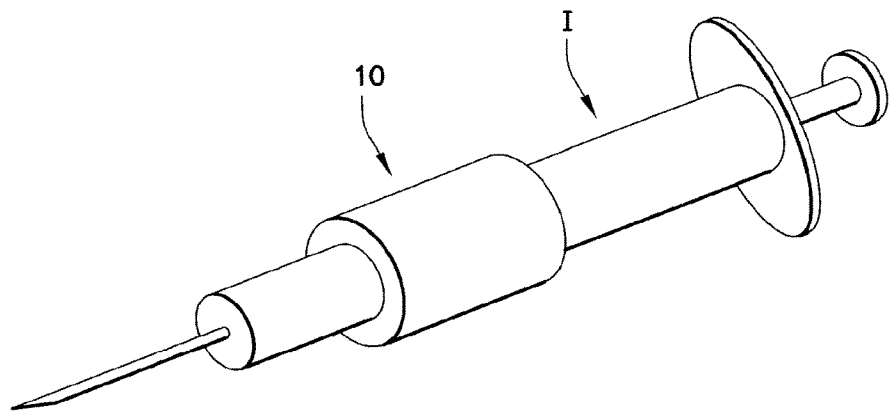
FIG. 1 is a perspective view of a needle assembly formed in accordance with the subject invention mounted onto an injector.
Figure 2:
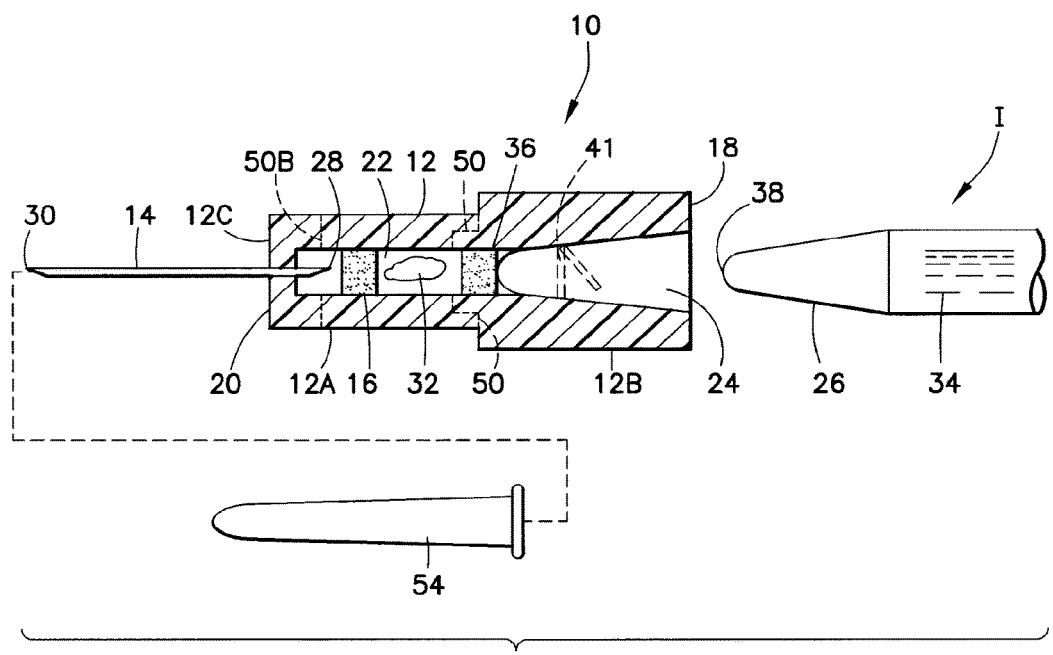
FIG. 2 is a cross-section of an embodiment of a needle assembly formed in accordance with the subject invention.
Figure 3:
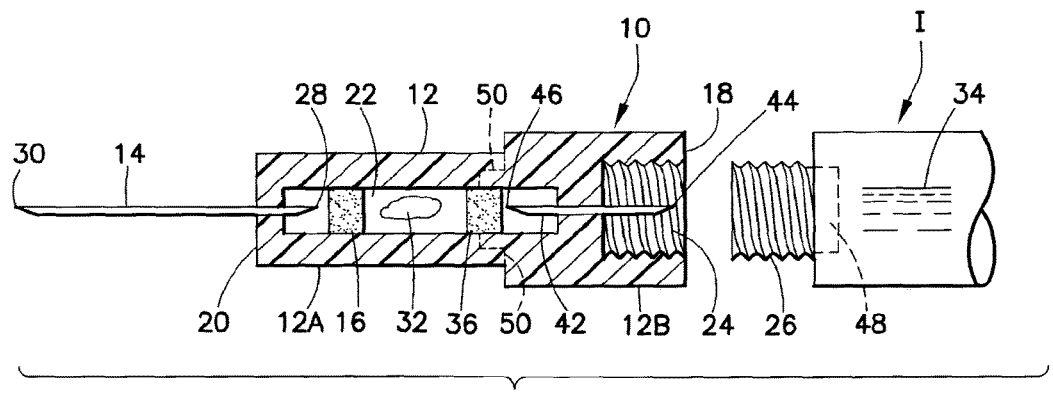
FIG. 3 is a cross-section of a second embodiment of a needle assembly formed in accordance with the subject invention.

With reference to the figures, a needle assembly 10 is provided herein formed to permit mixing of at least two substances in preparation for injection. The needle assembly 10 is formed as a stand-alone component which is mountable to a standard, un-modified medical injector, such as a syringe or pen injector. With reference to FIGS. 1 and 2, the needle assembly 10 is shown in connection with a medical injector I in the form of a syringe. In FIG. 3, the needle assembly 10 is shown in connection with the medical injector I being in the form of a pen injector. As will be appreciated by those skilled in the art, the medical injector I can be in the form of any known injector.

With reference to the figures, the needle assembly 10 generally includes a body 12, a needle 14, and at least one filter 16.

The body 12 includes a proximal end 18, a distal end 20 and a channel 22 located therebetween. The channel 22 may be located at any mid-point length of the body 12, and preferably extends through the proximal end 18 of the body 12 and distally therefrom. The body 12 may be formed of various materials, but is preferably formed of a material compatible with the substance to be contained therein, as described below. The body 12 may be formed of glass, thermoplastic, ceramic, metal and combinations thereof.

Preferably, the needle assembly 10 is removably mountable to the medical injector I. In this manner, the needle assembly 10 may be disposed of after use, particularly with the needle 14 being considered biohazardous. As being removably mountable, the medical injector I may be re-used with a subsequent needle assembly 10 or with a different needle assembly. This may be particularly desirable where the medical injector I is in the form of a pen injector. To permit removable mounting, one or more mounting features 24 may be formed on the body 12, particularly in proximity to the proximal end 18 thereof. As known in the art, the mounting features 24 may be in the form of a luer arrangement (FIG. 2) and/or a thread arrangement (FIG. 3). Cooperating features 26 may be formed on the medical injector I configured to coact with the mounting features 24 in having the needle assembly 10 be removably mounted onto the medical injector 10. The cooperating features 26 may be a luer and/or thread arrangement formed to cooperate with the mounting features 24. Other cooperating mounting arrangements permitting removal mounting known in the art may likewise be utilized. Alternatively, the body 12 may be rigidly fixed to the medical injector I, such as by fusion, adhesion, and/or mechanical connection. With fixed mounting, the needle assembly 10 will be disposed of with the medical injector I as a single-use device.

The needle 14 may be of any standard type and includes a proximal end 28 and a distal end 30, formed for insertion into a patient. The needle 14 is fixed to the body 12 with the distal end 30 extending distally from the distal end 20 of the body 12. The proximal end 28 is formed to be in communication with the channel 22.

The channel 22 is formed to accommodate at least one substance 32 intended for mixing with at least one other secondary substance. The substance 32 may be in dry form (powdered or granular) or in wet form (liquid or slurry) and may include one or more pharmaceutically-active agents. The substance 32 is intended for mixing with one or more secondary substances 34 accommodated in the medical injector I. With actuation of the medical injector I, the one or more secondary substances 34 are urged therefrom and into the needle assembly 10, particularly into the channel 22. Interaction of the substances 32, 34 results in mixing thereof as described below.

The filter 16 is porous and may be formed of any material compatible with the substance 32. The filter 16 is preferably located between the proximal end 18 of the needle 14 and the substance 32. With this arrangement, the filter 16 provides a barrier for the substance 32 and avoids compaction of the needle 14 into the substance 32. In addition, it is preferred that the filter 16 be configured so as to provide a barrier in maintaining the substance 32 within the channel 22. Thus, the overall porosity of the filter 16 should be configured to not permit passage therethrough of the substance 32. The porosity of the filter 16 may be configured based on various variables including pore size, length of the filter, extent of open/closed network of the pores and so forth.

Depending on how the needle assembly 10 is packaged, a porous second filter 36 may be provided in the channel 22 located proximally of the substance 32. The second filter 36 may be configured with the same considerations as noted above with respect to the filter 16. Alternatively, as discussed below, a film or other barrier may be applied across the channel 22 to provide a proximal barrier for the substance 32.

The filter 16 and the second filter 36 may be formed of various materials which are compatible with the substance 32. The needle assembly 10 may act as a storage container, where the substance 32 is maintained in the channel 22 for an extended period of time prior to use. With this arrangement, it is desired to have minimal, ideally no, chemical interactions between the filter 16/second filter 36 and the substance 32. The filter 16/second filter 36 may be formed of various materials, including, but not limited to thermoplastic, glass, ceramic, metal and combinations thereof. By way of non-limiting example, the filter 16 and the second filter 36 may be formed from a porous plastic filter, such as Porex porous filter (e.g., Catalogue No. X-5923, 18 to 40 micron std. pipette filter PE).

As indicated above, the substance 32 is maintained in the needle assembly 10 ready for mixing with the one or more secondary substances 34 located in the medical injector I. The one or more secondary substances 34 will be in a wet form (e.g., liquid or slurry) and selected to act as a diluent for, and/or as a compatible component as part of a multipart system with, the substance 32. With the needle assembly 10 being mounted to the medical injector I, the one or more secondary substances 34 may be urged from the medical injector I into the channel 22. With reference to FIG. 2, with the medical injector I being of a syringe type, the one or more secondary substances 34 may be urged directly from syringe tip 38 into the channel 22. Preferably, the second filter 36 is located between the substance 32 and the syringe tip 38.

The one or more secondary substances 34 are forced into the channel 22 under pressure generated by the medical injector I. The medical injector I generates pressure in administering the one or more secondary substances 34 as is well known in the art. The pressure generated by the medical injector I will urge the one or more secondary substances 34 towards the proximal end 28 of the needle 14. It is preferred that the filter 16, the channel 22, and the second filter 36 be configured to provide sufficient dwell time of the one or more secondary substances 34, with exposure to the substance 32, to ensure sufficient mixing prior to administration. If insufficient dwell time is provided, an insufficiently mixed solution may be administered.

Figure 4:
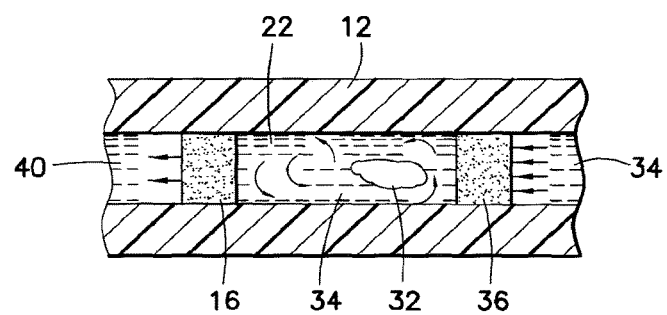
FIG. 4 is a schematic showing mixing of two substances in a needle assembly formed in accordance with the subject invention; and, FIG. 5 shows alternative configurations for a needle assembly formed in accordance with the subject invention.

In the preferred arrangement, it is preferred that the porosity of the second filter 36 be greater than the porosity of the filter 16. With reference to FIG. 4, with the second filter 36 be greater in porosity than the filter 16, the one or more secondary substances 34 may be urged through the second filter 36 more readily than through the filter 16. This will result in more restriction at the filter 16 than at the second filter 36. The level of restriction may be used to set the dwell time of the one or more secondary substances 34 in the channel 22. Accordingly, as represented by the arrows, the one or more secondary substances 34 will experience some turbulence in being exposed to the substance 32. The turbulence causes mixing of the substances 32, 34. With further pressure from the medical injector I during actuation, a mixed solution 40 will be caused to pass through the filter 16 with further passage through the needle 14 for administration. Mix characteristics of the substances 32, 34 (solubility, viscosity, etc.), as well as the physical dimensioning and configuration of the channel 22 and the filters 16, 36, must be considered in ensuring that sufficient mixing may be achieved in preparing the mixed solution 40 for administration.

Dwell time may be varied with variation in restriction to flow between the filter 16 and the second filter 36 as described above. Mixing may be conducted in-flow through the channel 22 as described above. In addition, or alternatively, a portion of the one or more secondary substances 34 may be urged into the channel 22 from the medical injector I without fully pressurizing the channel 22. In this manner, an amount of the one or more secondary substances 34 may be disposed into the channel 22 without any flow urged through the filter 16. The needle assembly 10 may be then agitated, e.g., by shaking or rolling, to cause mixing of the substances 32, 34. The medical injector I may then be caused to further urge the one or more secondary substances 34 therefrom in pressurizing the channel 22 and causing flow through the filter 16.

The substances 32, 34 may be mixed in-flow where all of the one or more secondary substances 34 are caused to be dispensed from the medical injector I in a continuous flow. The substances 32, 34 mix inside the channel 22 and the mixed solution 40 is administered. With in-flow mixing, it is preferred that the mixing be conducted with the needle 14 inserted into a patient for injection. Thus, for use, the needle assembly 10 is mounted on the medical injector I. The needle 14 is inserted into a patient, and the medical injector I is caused to be actuated. The medical injector I is configured such that, with an actuation of the medical injector I, a sufficient quantity of the one or more secondary substances 34 is urged from the medical injector I under sufficient pressure to cause sufficient mixing and administration of the mixed solution 40. Advantageously, the needle assembly 10 may be used with the medical injector I being in a standard, un-modified form to achieve mixing, including possible reconstitution.

Alternatively, the mixed solution 40 may be at least partially prepared prior to injection with the needle assembly 10 being mounted on the medical injector I. Here, sufficient quantity of the one or more secondary substances 34 may be urged from the medical injector I and into the channel 22. With agitation of the needle assembly 10 maintained on the medical injector I, sufficient mixing of the mixed solution 40 may be achieved prior to injection. Thereafter, the needle 14 may be inserted into a patient and injection administered.

Concerns may exist over gases trapped in the channel 22, particularly resulting from mixing. Vents may be provided on the in-flow mixing arrangement to allow release of any trapped gases from the channel 22 during injection. With the prior mixing arrangement, the medical injector I may be held in an upright position and partially activated to permit venting and achieve priming of the needle 14 prior to injection. Once primed, injection may be administered.

In-flow mixing or prior mixing may be selected based on the mix characteristics of the substances 32, 34. With the substance 32 being highly soluble (e.g., ALP powders), in-flow mixing may be utilized, whereas, with the substance 32 being less soluble, prior mixing may be utilized. ALP powders are ultra-light powders which may be formed by the process described in U.S. Published Appl. No. 2008/0226729 A1, the entire contents of which are incorporated by reference herein. Other powders, such as lyophilized powders, may be used with the subject invention.

With the medical injector I being of a syringe type, the second filter 36 need not be utilized. A removal barrier 41 (shown in dashed lines in FIG. 2), which may be in the form of a removable film, foil or plug, may be utilized to seal the proximal end of the channel 22 prior to use. In preparation for use, the removal barrier 41 is removed. The filter 16 provides restriction against flow, thus, permitting turbulence in mixing, as described above.

With reference to FIG. 3, the needle assembly 10 may be configured to be used with the medical injector I in the form of a pen injector. Here, a second needle 42 is provided having a proximal end 44 and a distal end 46. The second needle 42 is fixed to the body 12 with the distal end 46 being in communication with the channel 22. It is preferred that the second filter 36 be utilized with a pen injector configuration of the needle assembly 10 and that the second filter 36 be located between the substance 32 and the distal end 46 of the second needle 42. In this manner, compaction of the second needle 42 into the substance 32 may be avoided. Also, the second filter 36 acts as a proximal barrier for retaining the substance 32 within the channel 22.

The second needle 42 is configured so that the proximal end 44 has sufficient length to fully penetrate any septum 48 closing off the one or more secondary substances 34 in the medical injector I, with the needle assembly 10 being mounted to the medical injector I.

With the medical injector I in use as a pen injector, the one or more secondary substances 34 are urged through the second needle 42 and into the channel 22 during use. The substances 32, 34 mix in the same fashion as described above. The medical injector I may be of any standard, un-modified type and still be workable with the needle assembly 10.

To facilitate preparation of the needle assembly 10, it is preferred that the body 12 be modularly formed of at least two body components 12A, 12B. Preferably, the body components 12A, 12B are joined at a joint 50 located in the proximal back-half section of the channel 22. In this manner the fore body component 12A, which houses the distal section of the channel 22, may be prepared with the filter 16 and the substance 32. Thereafter, the second filter 36, if being used, may be disposed into the channel 22 in the fore body component 12A or into the channel 22 in the aft body component 12B. The fore and aft body components 12A, 12B are joined at the joint 50 using any known technique, such as by fusion, adhesion and/or mechanical connection. It is preferred that the joint 50 be at least liquid tight. The needle 14 and the second needle 42 may be fixed to the body components 12A, 12B in any sequence and with any known technique. Alternatively, the substance 32 may be disposed into the channel 22 in the aft body component 12B with the fore body component 12A being mounted thereto. It is further noted that the body 12 may be divided into further body components, such as tertiary body component 12C (FIG. 2), joined to the fore body component 12A at joint 50B. The tertiary body component 12C may have the needle 14 fixed thereto. As such, the needle 14 may be prepared and assembled separately from the substance 32 in the fore and aft body components 12A, 12B.

Figure 5:
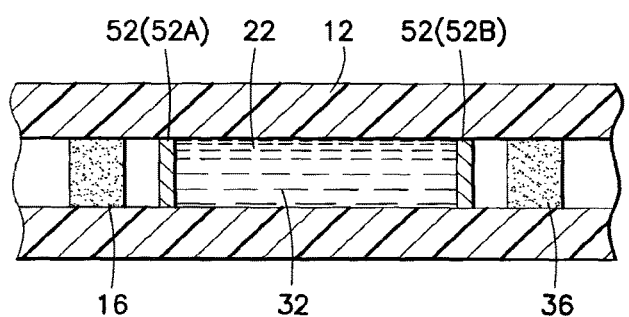

With reference to FIG. 5, one or more rupturable membranes 52 may be utilized in the channel 22 in lieu of, or in addition to, the filter 16 and the second filter 36. The rupturable membranes 52 may be utilized where the substance 32 is in a wet form (liquid or slurry).

The rupturable membranes 52 may be configured to rupture under pressure from the flow of the one or more secondary substances 34. The membranes 52 may be configured to readily rupture with turbulence being caused by the filter 16, with or without the second filter 36, as described above. Alternatively, the membranes 52 may be used in place of the filter 16 and/or the second filter 36 such that the rupture threshold of the respective membranes 52 is configured to provide equivalent resistance to flow in the same manner as the filter 16 and the second filter 36. For example, a first membrane 52A may be utilized alone in the channel 22, at the location of the filter 16, which is set to rupture upon a predetermined pressure build-up in the channel 22. This pressure build-up permits mixing of the substances 32, 34. With a second membrane 52B, the second membrane 52B may be configured to more readily rupture than the first membrane 52A; this provides an equivalent arrangement to the second filter 36 being more porous than the filter 16. If the membranes 52 are used in conjunction with the filter 16, and optionally the second filter 36, it is preferred that the membranes 52 provide the least resistance against flow through the channel 22. With this arrangement, the membranes 52 would readily rupture and permit the first filter 16 and the second filter 36, if used, to create turbulence in permitting mixing of the substances.

The membranes 52 are liquid impervious and may be formed of various rupturable materials, such as films and/or foils. The membranes 52 may be utilized to contain the substance 32 within the needle assembly 10. This is particularly useful where the substance 32 is in wet form.

The needle assembly 10 may also include a needle shield 54 formed to cover the distal end 30 of the needle 14 when not in use. The needle shield 54 may cover the distal end 30 before and/or after use of the needle 14. The needle shield 54 may be formed with any known configuration and may have releasable mounting features for releasably retaining onto the body 12 and/or the needle 14. For example, the needle shield 54 may include an elastomeric inner liner into which the needle 14 is embedded with the needle shield 54 being mounted thereabout. In addition, or alternatively, the needle shield 54 may include mounting features, such as detents or grooves, which permit snap mounting onto the body 12.

What is claimed is:

1. A needle assembly comprising:
    a body having a proximal end, a distal end, and a channel located therebetween, the body being configured to be mounted to an injector;
    a needle fixed to the body, the needle having proximal and distal ends, the distal end extending distally from the distal end of the body and being formed for insertion into a patient, the proximal end of the needle being in communication with the channel; and
    a first porous filter disposed in the channel proximally of the proximal end of the needle; and
    a second porous filter disposed proximally of the first porous filter in the channel and separated from the first porous filter, forming a chamber therebetween;
    wherein at least one of the first and second porous filters is fixedly disposed within the channel.

2. The needle assembly of claim 1, wherein the first and second porous filters are fixedly disposed within the channel.

3. The needle assembly of claim 1, wherein the second porous filter is more porous than the first porous filter.

4. The needle assembly of claim 1, further comprising a shield to cover the distal end of the needle.

5. The needle assembly of claim 1, further comprising one or more mounting features to removably attach the body to an injector.

6. The needle assembly of claim 5, wherein the mounting features include one or more selected from the group consisting of:
    a luer arrangement;
    a threaded arrangement; and
    combinations thereof.

7. The needle assembly of claim 1, further comprising a second needle fixed to the body, the second needle having proximal and distal ends, the distal end of the second needle being in communication with the channel.

8. The needle assembly of claim 1, further comprising a drug substance disposed in the channel between the first and second porous filters.

9. The needle assembly of claim 1, further comprising a barrier disposed proximally of the second porous filter to selectively seal a proximal end of the channel.

* * * * *